United States Patent
Bilodeau et al.

(10) Patent No.: US 10,281,366 B2
(45) Date of Patent: May 7, 2019

(54) SAMPLING DEVICE INCLUDING MECHANICAL FORCE FEEDBACK MECHANISM

(71) Applicant: Rapiscan Systems, Inc., Torrance, CA (US)

(72) Inventors: James P. Bilodeau, Gardner, MA (US); Thomas A. Hagerty, Melrose, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 202 days.

(21) Appl. No.: 15/374,333

(22) Filed: Dec. 9, 2016

(65) Prior Publication Data

US 2018/0164189 A1   Jun. 14, 2018

(51) Int. Cl.
*G01N 1/20* (2006.01)
*G01N 1/02* (2006.01)

(52) U.S. Cl.
CPC ......... *G01N 1/02* (2013.01); *G01N 2001/022* (2013.01); *G01N 2001/028* (2013.01)

(58) Field of Classification Search
CPC ............... G01N 1/02; G01N 2001/022; G01N 2001/028; G01N 1/22; A61B 17/3207; A61B 5/1411; A61B 5/150251; G02N 21/63

See application file for complete search history.

(56) References Cited

U.S. PATENT DOCUMENTS

| | | | |
|---|---|---|---|
| 7,060,223 B2 | 6/2006 | DiCesare et al. | |
| 7,421,912 B2 | 9/2008 | Nacson et al. | |
| 8,858,582 B2 | 10/2014 | Schiff et al. | |
| 2012/0204659 A1* | 8/2012 | Fine | G01N 1/02 73/864 |
| 2014/0073990 A1* | 3/2014 | Holmes | B01L 3/502 600/575 |

* cited by examiner

*Primary Examiner* — Lisa M Caputo
*Assistant Examiner* — Nigel H Plumb
(74) *Attorney, Agent, or Firm* — Novel IP (57) ABSTRACT

The present disclosure includes a sampling device for collecting a sample from a target surface, the sample device including a handle, a body extending from the handle, and a mechanical force feedback mechanism. The mechanical force feedback mechanism is configured to change an orientation of the body relative to the handle when force is applied to a target surface by the sampling device.

18 Claims, 7 Drawing Sheets

SAMPLING DEVICE INCLUDING MECHANICAL FORCE FEEDBACK MECHANISM

BACKGROUND

The embodiments described herein relate generally to sampling devices, and more specifically, to a sampling device including a mechanical force feedback mechanism.

Screening systems for threat compounds such as explosives as well as chemical and biological weapons are commonly used. These screening systems must be able to collect, concentrate, and analyze trace samples quickly and accurately. Many detection technologies such as mass spectrometry (MS), ion mobility spectrometry (IMS), gas chromatography (GC), optical spectroscopy, have been developed to detect a wide range of explosives and chemical weapons, and, to a lesser extent, biological weapons. The precision of a trace detector is an important factor in minimizing false positive rates. However, collecting enough of a sample to deliver to the trace detector is an important factor in maximizing detection rates, because if a trace sample is not appropriately delivered to the detector, a "non-detect event" may occur. In at least some cases, collection and delivery of samples to these trace detectors is difficult, as methods of collection and delivery must adapt to a wide range of applications and screening scenarios.

Certain contraband substances—such as explosive or narcotics—are difficult to detect in trace amounts. Security screenings for high traffic areas, such as an airport, attempt to identify and detain individuals involved with contraband substances by collecting samples from the body or clothing. Due to the high traffic nature of these security screenings, the screenings need to be both quick and accurate.

One type of sampling method involves using hand-held detection devices. These devices, usually in the form of a "wand", are easy to handle, provide a suitable distance between the user and the target surface to avoid cross-contamination, and simplify sample transfer to an analytical device. However, these devices generally require the application of a particular amount of force or pressure in order to obtain a sufficient amount of sample from the target surface. Sufficient collection of a sample increases the probability of detecting a trace material within the sample, and the trace detection rate decreases when a user does not apply enough force or pressure against the target surface.

BRIEF DESCRIPTION

In one aspect, a sampling device for collecting a sample from a target surface is provided. The sample device includes a handle, a body extending from the handle, a sampling head opposite the handle, and a mechanical force feedback mechanism. The mechanical force feedback mechanism is configured to change an orientation of the body relative to the handle when force is applied to a target surface by the sampling device.

In another aspect, a method of using a mechanical force feedback sampling device is provided. The method includes grasping a handle of a sampling device, applying a force against a target surface using the sampling device, increasing the applied force to a threshold amount of force such that a mechanical force feedback mechanism induces a change in the orientation of the sampling device, and collecting a sample.

In yet another aspect, a sampling device for collecting a sample from a target surface is provided. The sampling device includes a handle and a body comprising an end. The body is coupled to the handle. The sampling device also includes sampling head opposite the handle. The sampling head comprises a support surface configured to support a sampling trap. The sampling device further includes a mechanical force feedback mechanism configured to indicate when a threshold amount of force is applied to a target surface by the sampling device.

DETAILED DESCRIPTION

The embodiments disclosed herein provide a sampling device configured to facilitate improved detection of trace contraband materials using a mechanical force feedback mechanism to ensure that the user achieves a threshold amount of force required to collect a sample. In particular, a sampling head of the sampling device is placed against a target surface to collect the sample, and force is applied by the user until the mechanical force feedback mechanism indicates to the user that the threshold amount of force has been applied. More particularly, in the exemplary embodiment, the mechanical force feedback mechanism induces a geometric or orientation change of the sampling device when a threshold amount of force is exerted by the sampling device on the target surface. The sample may then be transferred to an analysis device. The sampling device, and the method of using the sampling device, facilitates reduced sampling error during both the collection and transfer of sampled material.

Figure 1:
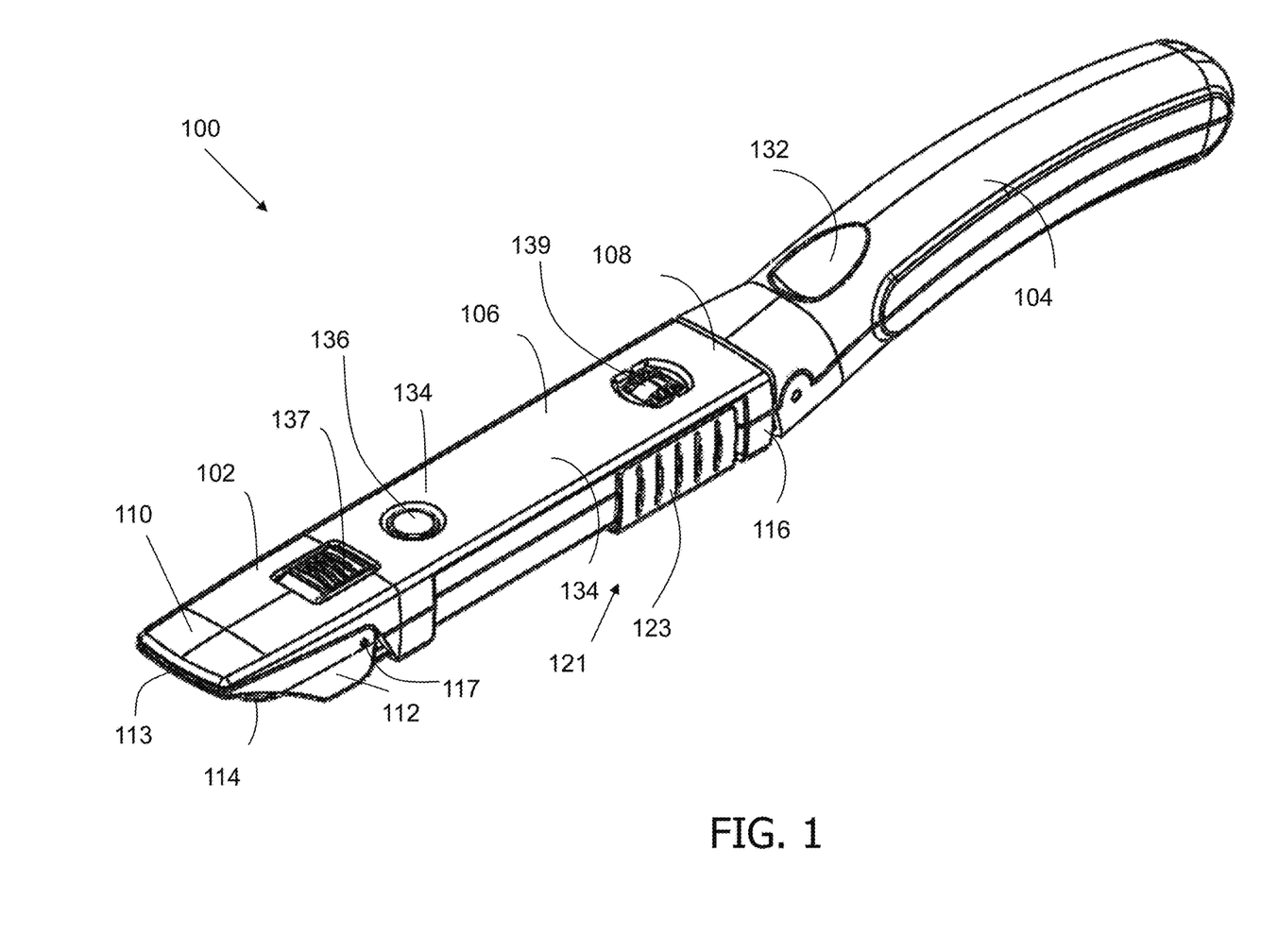
FIG. 1 is a perspective view of an exemplary embodiment of a sampling device.
Figure 2:
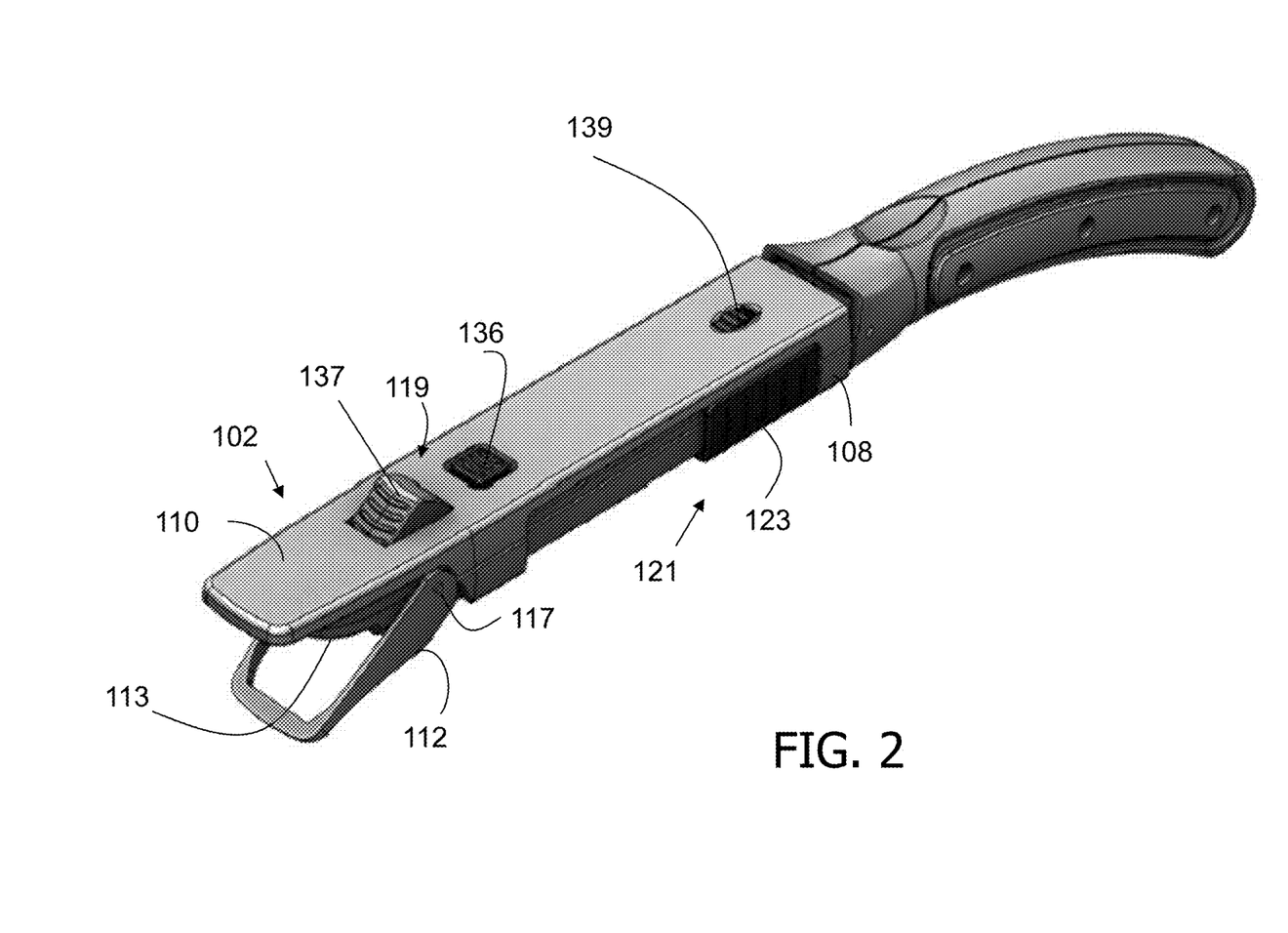
FIG. 2 is a perspective view of the sampling device shown in FIG. 1 with a frame in an opened configuration suitable to receive a trap holder.
Figure 3:
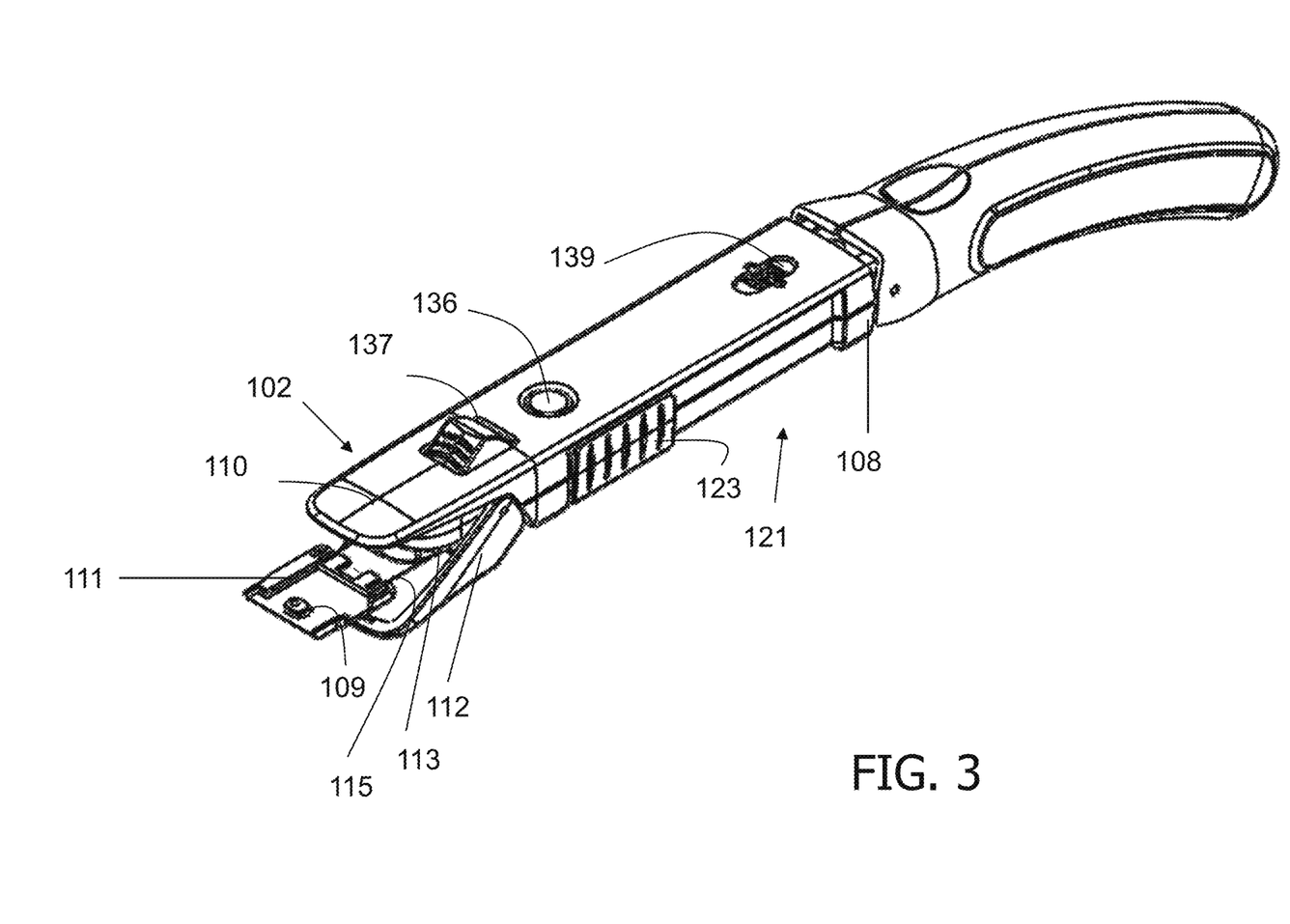
FIG. 3 is a perspective view of the sampling device shown in FIGS. 1 and 2 with a trap holder coupled to a body of the sampling device.

FIGS. 1-3 are perspective views of an exemplary embodiment of a sampling device 100. In a first embodiment, sampling device 100 includes a handle 104, a body 106, and a sampling head 102. Body 106 includes a first or proximal end 108 and a second or distal end 110 opposite first end 108. Handle 104 is coupled to first end 108 of body 106. Sampling head 102 is located at distal end 110 of body 106. Sampling head 102 includes a trap holder 111, a frame 112, a support surface 113, and a sample trap 114. A coupling mechanism 115 couples trap holder 111 to body 106. In the illustrated embodiment, coupling mechanism 115 includes a band or strap. Trap holder 111 is configured to retain sample trap 114, such as a fiberglass sample trap. Sample trap 114 is configured to collect a sample from the target surface. In the illustrated embodiment, sample trap 114 is removably coupled to trap holder 111 such that sample trap 114 may be removed from sampling device 100 after sample trap 114 has been used for collection of one or more samples. In one embodiment, trap holder 111 includes a peg 109 with a retention mechanism having a mushroom shape, or any other shape that retains sample trap 114 or trap holder 111. An opening (not shown) in sample trap 114 is aligned with peg 109 and pushed down over peg 109. The shape of peg 109 keeps sample trap 114 in place on trap holder 111. Trap holder 111 may support various types, sizes, and shapes of sample traps 114. Support surface 113 is configured to maintain a position of sampling trap 114 during collection of a sample and may include a relatively soft or padded surface or a relatively rigid surface.

Figure 4:
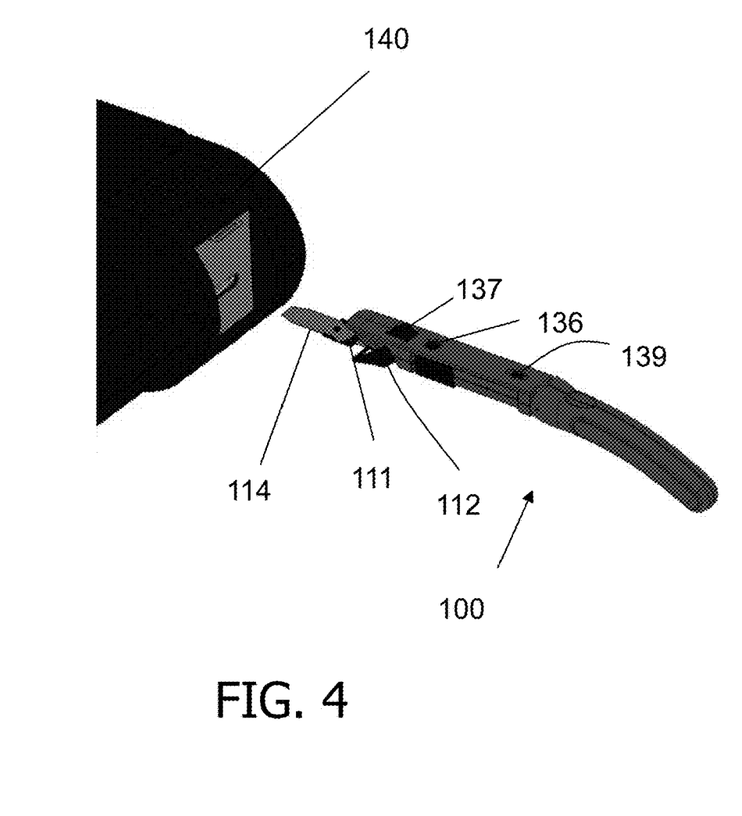
FIG. 4 is a perspective view of the sampling device shown in FIGS. 1-3 and an analysis device.
Figure 5:
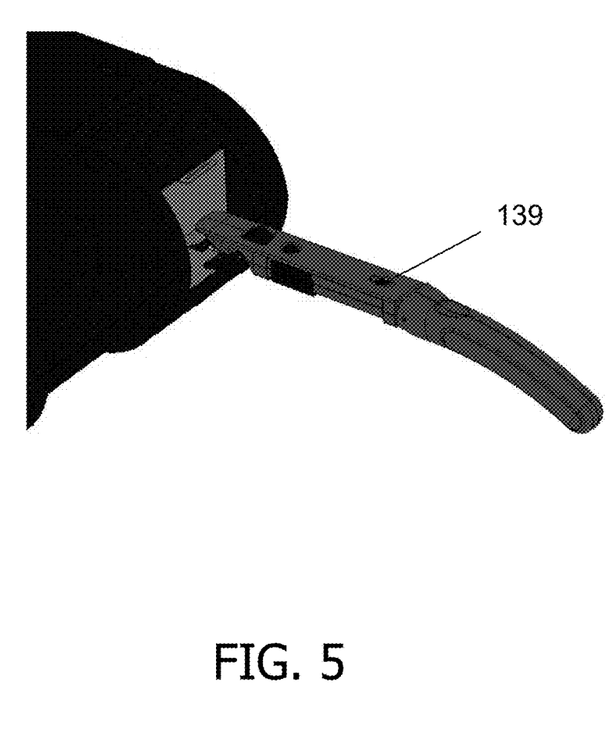
FIG. 5 is a perspective view of the sampling device and analysis device shown in FIG. 4, wherein a trap holder is inserted into the analysis device.

A pin 117 couples frame 112 to distal end 110 of body 106, such that frame 112 is pivotable between a closed position (see FIG. 1), in which frame 112 couples sample trap 114 against support surface 113, and an open position (see FIGS. 2 and 3), in which sample trap 114 may be inserted into (or removed from) sampling device 100 and/or may be inserted into an analysis device (see FIGS. 4 and 5). Frame 112 is configured to maintain sample trap 114 in a position suitable for sample collection when frame 112 is in the closed position. Moreover, frame 112 may be adjustable to accommodate the different sizes of sample traps 114. In an embodiment, frame 112 is adjustable depending on the size of sample trap 114 to ensure a secure fit. Sampling device 100 includes a frame adjustment mechanism 119 to transition frame 112 between the closed position and the open position. In the illustrated embodiment, frame adjustment mechanism 119 includes a button 136 and a latch 137 located on body 106. Button 136 and latch 137 extend from body 106. When force is exerted upon button 136, frame adjustment mechanism 119 causes frame 112 to transition into the open position, which in turn causes latch 137 to extend outwardly from sampling head 102. In this embodiment, once frame 112 is open, sample trap 114 may be coupled to trap holder 111 or removed from trap holder 111. Depressing latch 137 causes frame 112 to transition into the closed position.

In addition, sampling device 100 includes a trap holder adjustment mechanism 121. Trap holder adjustment mechanism 121 is configured to transition trap holder 111 from an internal position (see FIGS. 1 and 2), in which trap holder 111 is positioned inside of body 106, and an external position (see FIG. 2), in which trap holder 111 is external to body 106 to facilitate insertion/removal of sample trap 114 and/or analysis of a sample collected on sample trap 114. In the illustrated embodiment, trap holder adjustment mechanism 121 includes a slide mechanism 123 disposed on body 106. When slide mechanism 123 is moved towards distal end 110 of body 106, trap holder 111 (and/or coupling mechanism 115) are in turn moved forward, such that trap holder 111 is transitioned to the external position. Sample trap 114 may then be coupled to or removed from trap holder 111 or inserted into an analysis device. When slide mechanism 123 is moved towards proximal end 108 of body 106, trap holder 111 is transitioned to the internal position. In the illustrated embodiment, when trap holder 111 is transitioned back to the internal position, latch 137 is depressed to transition frame 112 to the closed position, in which sample trap 114 is retained, or locked, against support surface 113.

FIGS. 4 and 5 are perspective views of sampling device 100 and an analysis device 140. Frame 112 is in the open position, and trap holder 111 is in the external position, such that sample trap 114 is extended towards analysis device 140. Analysis device 140 may be any device suitable to test a sample, such as, but not limited to, an itemizer desorber. As shown in FIG. 5, sample trap 114 is inserted into analysis device 140 for analysis of any sample collected on sample trap 114 as sampling device 100 is advanced toward analysis device 140, until distal end 110 of body 106 contacts analysis device 140. In another embodiment, sampling device 100 is advanced toward analysis device 140 after sample trap 114 is initially inserted into analysis device 140, until sample trap 114 contacts analysis device 140. In an alternative embodiment, sample trap 114 and/or trap holder 111 are removed from sampling device 100 to insert sample trap 114 and/or trap holder 111 into analysis device 140. After the sample is analyzed, if no contraband material is detected, sample trap 114 is retracted back into sampling device 100. More particularly, slide mechanism 123 is moved towards proximal end 108 of body 106 to retract trap holder 111, thereby retracting sample trap 114, and latch 137 is depressed to transition frame 112 into the closed position to couple sample trap 114 against support surface 113 for re-use. In the illustrated embodiment, sampling device 100 further includes a counter or dial 139. Turning dial 139 adjusts a number displayed (e.g., on dial 139 and/or on a display adjacent thereto), indicating a number of times sample trap 114 has been used. Used sample traps 114 are removed from sampling device 100 either after a contraband material has been detected or sample trap 114 has been used a predetermined number of times (e.g., 5 times, 10 times, 20 times, etc.).

Figure 6:
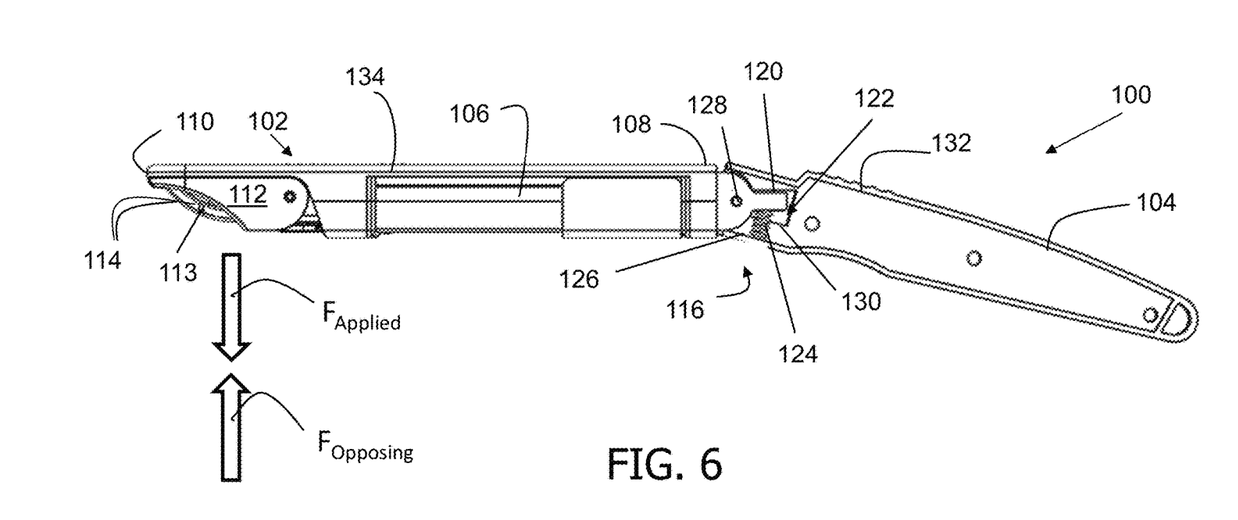
FIG. 6 is cross-sectional diagram of an exemplary embodiment of a sampling device in a first configuration.
Figure 7:
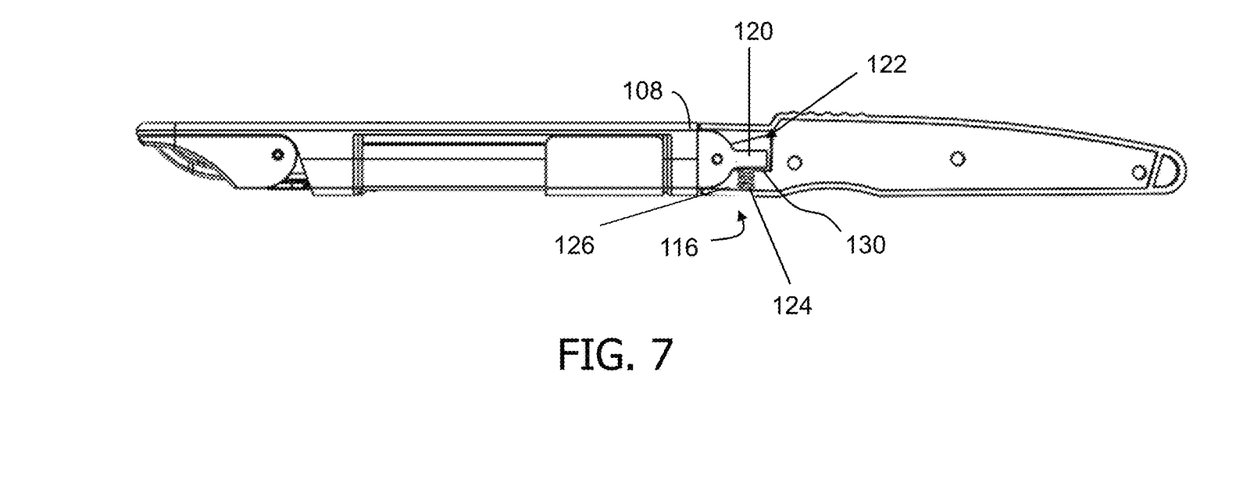
FIG. 7 is a cross-sectional diagram of the sampling device shown in FIG. 6 in a second configuration.

FIG. 6 is cross-sectional diagram of one embodiment of sampling device 100 in a first configuration, also referred to herein as an at rest configuration. FIG. 7 is a cross-sectional diagram of sampling device 100 in a second configuration, also referred to herein as a threshold configuration. Sampling device 100 transitions from the at rest configuration to the threshold configuration when a specific threshold amount of force is exerted upon a target surface by sampling device 100.

Sampling device 100 further includes a mechanical force feedback mechanism 116, which, in the illustrated embodiment, includes a rotational junction between handle 104 and body 106. More particularly, handle 104 includes a cavity 122 and body 106 includes an arm 120 extending from first end 108 into cavity 122. In an alternative embodiment, body 106 includes cavity 122 and handle 104 includes arm 120 extending from cavity 122. In addition, mechanical force feedback mechanism 116 includes a biasing member 124 extending between arm 120 and an interior wall 126 of handle 104. In the exemplary embodiment, biasing member 124 is a spring. More specifically, spring 124 is at least one of a leaf spring, a compression spring, an extension spring, a torsion spring, a disc spring, an air spring, a gas spring, a flat spring, an elastomeric spring, or a constant force spring. In some embodiments, mechanical force feedback mechanism 116 includes a plurality of springs 124.

Cavity 122 is sized to allow arm 120 to rotate within cavity 122. More specifically, a pin 128 couples arm 120 to first end 108 of handle 104, enabling body 106 to rotate, relative to handle 104. Mechanical force feedback mechanism 116 is thus configured to facilitate rotation of body 106 relative to handle 104 about pin 128 when sufficient force is applied using sampling device 100 on the target surface. More specifically, in the illustrated embodiment, when a force $F_{Applied}$ is applied by sampling device 100 against a target surface, an opposing force $F_{Opposing}$ is exerted by the target surface. As arm 120 rotates about pin 128, the distance between arm 120 and interior wall 126 of sampling device 100 is decreased, thereby compressing spring 124.

Mechanical force feedback mechanism 116 is further configured to prevent further rotation of body 106 when a threshold amount of force is applied. If less force than the threshold amount of force is applied to the target surface, the sample may not be fully collected. In one embodiment, the threshold amount of force is at least about one pound of force. In an alternative embodiment, the threshold amount of force is at least about two pounds of force. In another alternative embodiment, the threshold amount of force is about a half pound of force. Additionally or alternatively, mechanical force feedback mechanism 116 may be configured such that, when the threshold amount of force is applied, arm 120 contacts a shoulder 130 within cavity 122, preventing further rotation of arm 120. In the illustrated embodiment, once the threshold amount of force is applied, body 106 is substantially parallel to handle 104, and sampling device 100 is in the threshold position. The transition of sampling device 100 to the threshold configuration provides a visual indicator or feedback to the user that the threshold amount of force has been applied.

Figure 8:
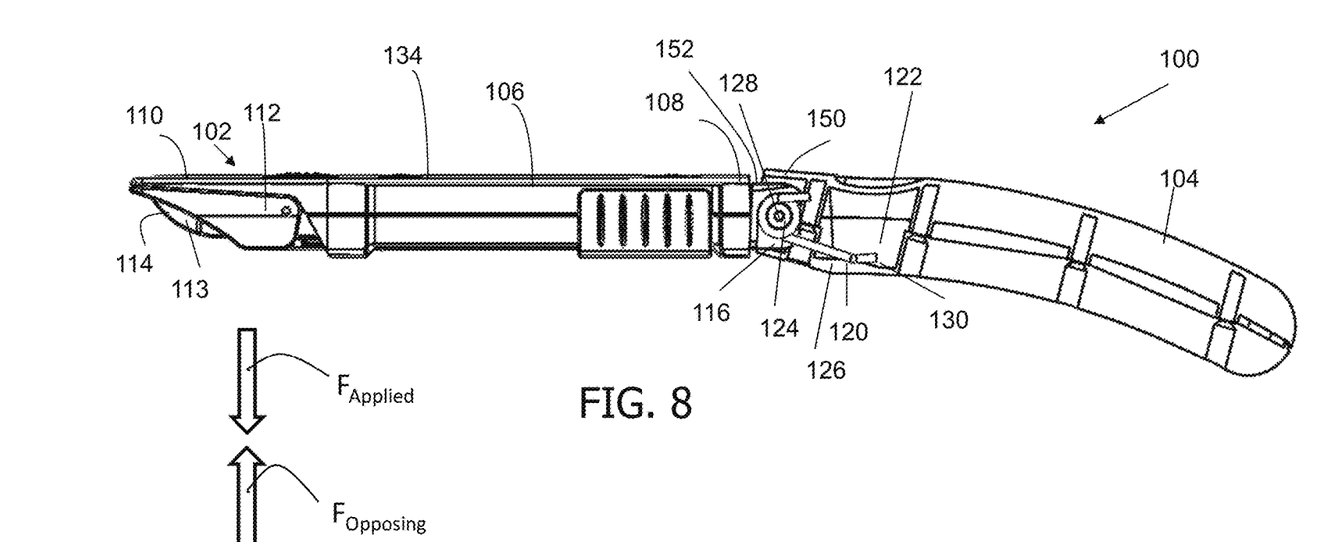
FIG. 8 is a cross-sectional diagram of an alternative embodiment of a sampling device in a first configuration.
Figure 9:
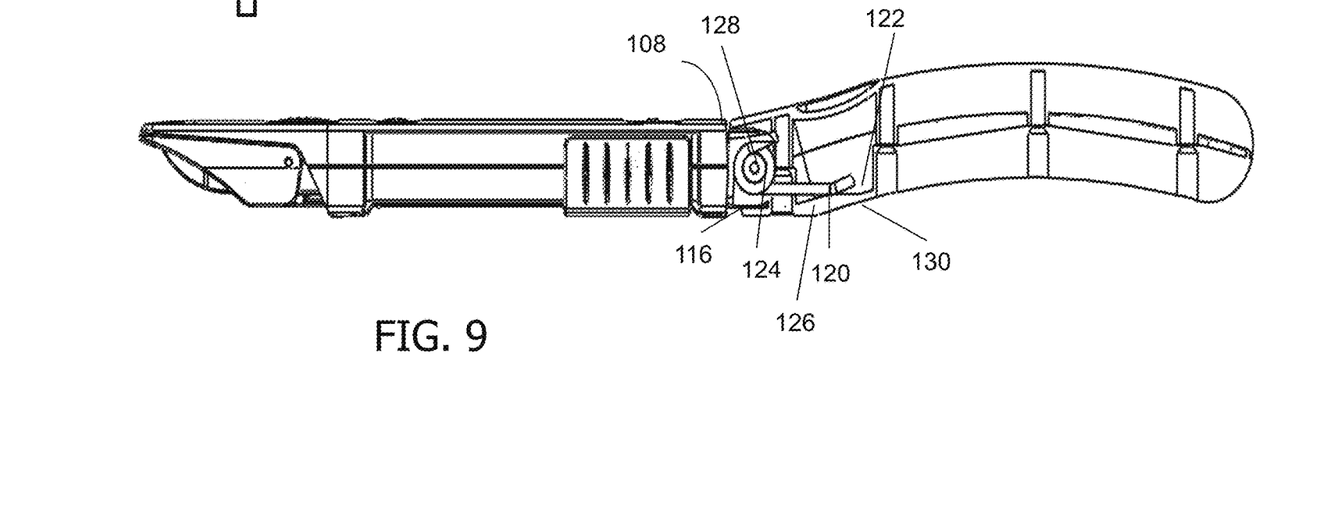
FIG. 9 is a cross-sectional diagram of the alternative embodiment of the sampling device shown in FIG. 8 in a second configuration.

FIG. 8 is a cross-sectional diagram of an exemplary embodiment of sampling device 100 in the first or at rest configuration, and FIG. 9 is a cross-sectional diagram of sampling device 100 shown in FIG. 8 in the second configuration. In this embodiment, biasing member 124 is at least one torsion spring wrapped around pin 128. When force $F_{Applied}$ is applied by sampling device 100 against a target surface, an opposing force $F_{Opposing}$ is exerted by the target surface. Handle 104 pushes against a torsion arm 138 of the torsion spring, causing the torsion spring to tighten, which enables body 106 to move relative to handle 104. Mechanical force feedback mechanism 116 is configured such that, when the threshold amount of force is applied, an external wall 150 of handle 104 contacts an interface wall 152 of body 106, thereby preventing further rotation of body 106.

Figure 10:
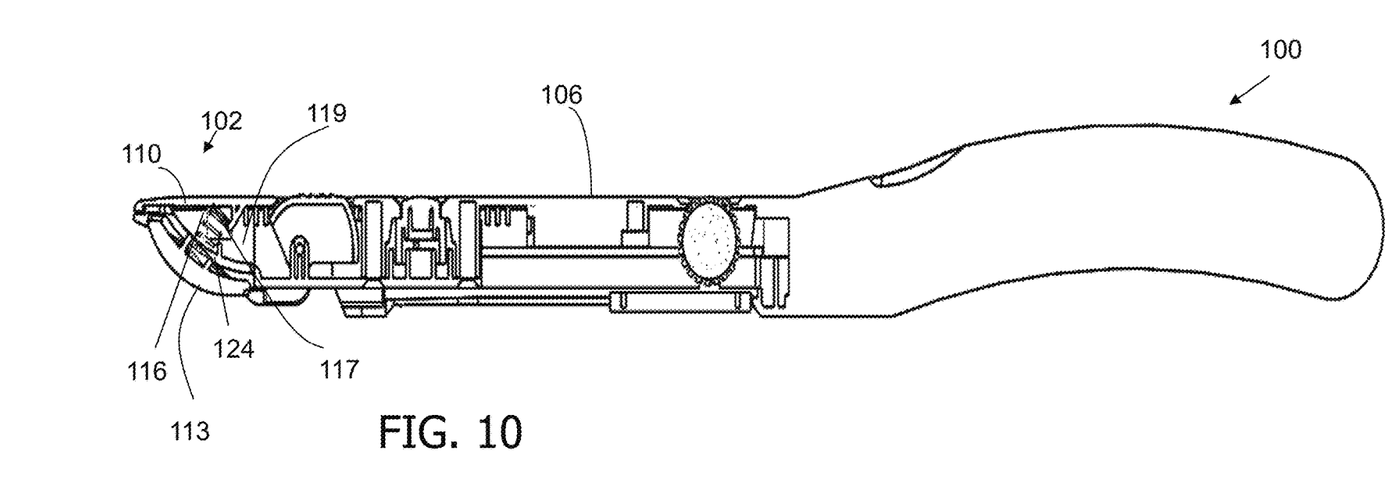
FIG. 10 is a cross-sectional diagram of another alternative embodiment of a sampling device in a first configuration.
Figure 11:
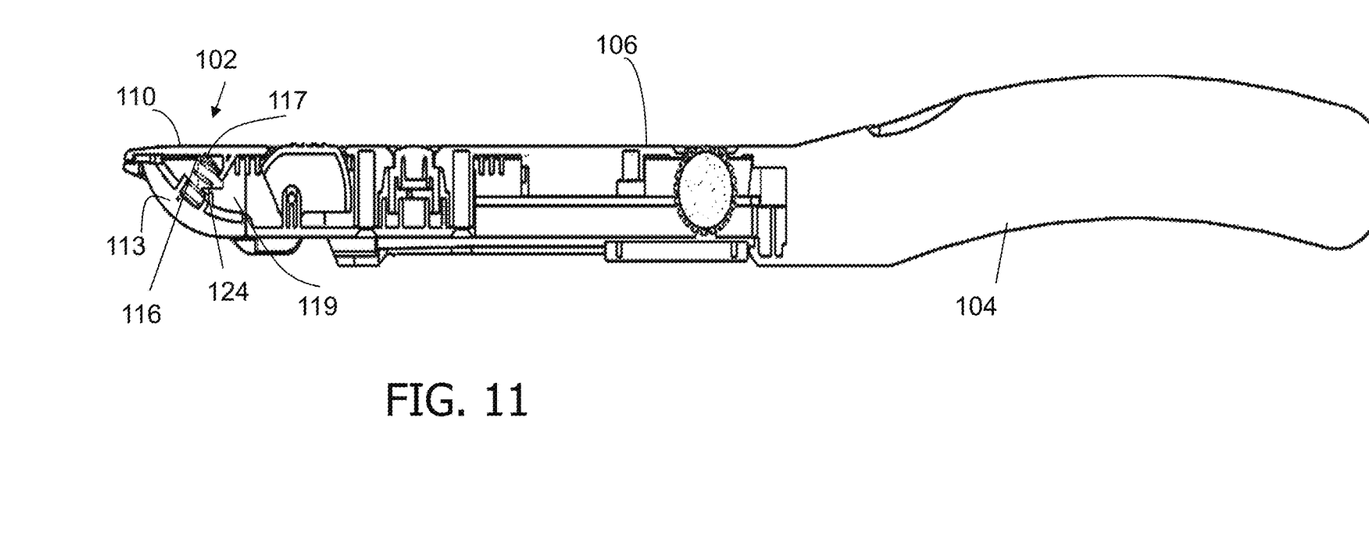
FIG. 11 is a cross-sectional diagram of the alternative embodiment of sampling device shown in FIG. 10 in a second configuration.

FIG. 10 is a cross-sectional diagram of another alternative embodiment of sampling device 100 in the first or at rest configuration, and FIG. 11 is a cross-sectional diagram of sampling device 100 shown in FIG. 10 in the second or threshold configuration. In this embodiment, mechanical force feedback mechanism 116 is located within sampling device 100 at distal end 110 of body 106. Biasing member 124 is coupled to a sampling surface 113 and a body interior 117, and housed within a distal cavity 119. Biasing member 124 transitions from an extended configuration to a compressed configuration when force is applied to the target surface by sampling device 100. Moreover, the compressing of bias member 124 causes sampling surface 113 to compress inward toward distal cavity 119. In an embodiment, sampling device 100 includes at least one of the force indicators described below.

In an alternative embodiment, mechanical force feedback mechanism 116 includes a rotational junction between sampling head 102 and body 106. When force is applied by sampling device 100 against a target surface, mechanical force feedback mechanism 116 induces a change in orientation of sampling head 102 relative to body 106, for example, using biasing member 124 as described herein. In this embodiment, the orientation of body 106 relative to handle 104 does not change.

In one embodiment, mechanical force feedback mechanism 116 is further configured to provide tactile feedback to the user. When the threshold amount of force is applied, mechanical force feedback device 116 provides the tactile feedback to the user. In an embodiment, the engagement of arm 120 with shoulder 130 and/or the engagement of external wall 150 with interface wall 152 causes the user to feel the completion of the transition between the resting configuration and the straightened configuration.

In the exemplary embodiment, sampling device 100 is configured as a wand, wherein sampling head 102 is coupled to handle 104. Handle 104 is also configured for easy manipulation of the sample head for both collection of the sample and transfer of the sample for analysis. In some embodiments, handle 104 includes one or more grooves 132 on at least a portion thereof, to enable an improved and more secure grip on sampling device 100. Grooves 132 may further function as a placement indicator, to indicate to the user a location where their hand should be placed on handle 104 to exert the threshold amount of force upon the target surface by sampling head 102. In alternative embodiments, handle 104 includes no grooves but instead includes one or more flat surfaces. A lower portion of handle 104 includes one or more arches, which may further improve a user's grip on sampling device 100 and/or serve as an additional placement indicator. In one embodiment, handle 104 further includes a strap to secure the user's grip.

In some embodiments, sampling device 100 is further configured to provide a force indicator to signal to the user when the threshold amount of force is applied to the target surface as an additional feedback mechanism. In one embodiment, the force indicator is an audible indicator that provides a clicking sound, and sampling device 100 is configured to provide the clicking sound when rotation of body 106 relative to handle 104 causes sampling device 100 to move to the threshold configuration. It should be understood that other audible indicator mechanisms can be used in connection with sampling device 100.

In another embodiment, the force indicator is a visual force indicator that visually indicates when a threshold amount of force has been applied by sample device 100 to the target surface. In this embodiment, the visual force indicator includes a pop-up member (not shown) coupled to body 106 or handle 104, wherein the member pops up to visually indicate to the user when the threshold force is applied.

In another embodiment, the force indicator is a color band only visible when the sampling device 100 is in the at rest configuration. The color band may be located on a portion of the handle 104 that is exposed when sampling device 100 is in the at rest configuration. In one embodiment, the color band is located on interface wall 152. In an alternative embodiment, the color band is located on a portion of the body 106 that is exposed when sampling device 100 is in the at rest configuration. When the threshold amount of force is applied, handle 104 and body 106 make contact, and handle 104 covers the exposed color band resulting in the color band no longer being exposed, visually indicating that sufficient force has been used. In an alternative embodiment, the visual indicator includes numbers and/or letters. It should be understood that other visual force indicators can be used in connection with the device.

In an embodiment, sampling device 100 further includes an over-force indicator (not shown). The over-force indicator indicates when a predetermined amount of force that is greater than the threshold amount of force has been applied. In an embodiment, the predetermined amount of force is greater than the threshold amount of force, preventing the application of an amount of force that can potentially damage the target surface and/or sampling device 100. In some embodiments, the over-force indicator includes a mechanism that enables a portion of sampling device 100 to break away when the predetermined amount of force is applied, and/or an audible and/or visual alarm. In one embodiment, the predetermined amount of force for the over-force indicator is within a range of about 3 to about 5 pounds. It should be understood that different embodiments of the sampling device have different over-force indicator ranges depending on, for example, sampling device design, weight, and/or the nature of the target surface.

In one embodiment, at least a portion of exterior 134 of sampling device 100 includes a protective shell (not shown). The shell may be fabricated from a material suitable to protect an interior of sampling device 100 from physical damage. Physical damage may include but is not limited to dropping of sampling device 100, excess force applied by or against sampling device 100, dust, and water. The protective shell may encapsulate exterior 134 of sampling device 100. Alternatively, the protective shell may encapsulate only a portion of sampling device 100. The protective shell may be fabricated from at least one of rubber, plastic, metal, silicon, and/or any other suitable material. Additionally or alternatively, a handle shell (not shown) may surround at least a portion of handle 104, wherein the handle shell is made of a material that simultaneously protects handle 104 and allows for suitable grip thereon. The handle shell may be fabricated from but is not limited to at least one of silicone, rubber, plastic, and metal.

Sampling device 100 is configured to collect samples including but not limited to at least one of an explosive, an energetic material, a taggant, a narcotic, a toxin, a chemical warfare agent, a biological warfare agent, a pollutant, a pesticide, a toxic industrial chemical, a toxic industrial material, a homemade explosive, a pharmaceutical trace contaminant, a biomarker for medical applications, a chemical marker for medical applications, a biomarker for clinical hygienic applications, a chemical marker for clinical hygienic applications, and combinations thereof.

Sampling device 100 described herein can be used in conjunction with various imaging-based security apparatus. Imaging-based security systems may include but are not limited to a millimeter wave system, an X-ray backscatter system, and/or any other suitable security system. Such imaging-based security apparatus, when used for security screening, provide images of articles that may be hidden under a passenger's clothes. When such a hidden article is identified under the clothes, an analysis is performed to determine the nature of the hidden article.

Sampling device 100 described herein can be utilized to collect adequate samples of explosives on baggage, cargo, and personnel due to concealed explosive devices. Trace contamination is known to be pervasive throughout the bomb making and bomb packing process. This contamination can take the form of vapor for more volatile explosives (e.g., the class of nitrate esters and nitro toluenes, as well as taggant compounds) or particles for the more crystalline forms (e.g., the nitramines RDX and HMX).

While certain exemplary embodiments have been described and shown in the accompanying drawings, it is to be understood that such embodiments are merely illustrative of and not restrictive on the broad disclosure, and that this disclosure not be limited to the specific constructions and arrangements shown and described, since various other modifications may occur to those ordinarily skilled in the art.

What is claimed is:

1. A sampling device for collecting a sample from a target surface, the sampling device comprising:
 a handle;
 a body extending from said handle;
 a sampling head opposite said handle; and
 a mechanical force feedback mechanism configured to change an orientation of said body in relation to said handle when force is applied to the target surface by said sampling device, wherein the mechanical force feedback mechanism is defined by a rotational junction connecting the body to the handle, wherein the rotational junction comprises a cavity defined in an interior of one of the handle and the body, an arm extending from the other of the handle and the body and into the cavity, and a biasing member extending between the arm and an interior wall defining the cavity, and wherein the arm rotates in relation to the interior wall when force is applied to the target surface by said sampling device.

2. The sampling device according to claim 1, wherein said rotational junction comprises a pin about which said body rotates in relation to said handle when force is applied to the target surface by said sampling device.

3. The sampling device according to claim 1, wherein said mechanical force feedback mechanism prevents further rotation of said body in relation to said handle when a threshold amount of force to the target surface is applied by said sampling device.

4. The sampling device according to claim 1, wherein said mechanical force feedback mechanism operatively couples said handle to said body.

5. The sampling device according to claim 1, wherein said sampling head comprises a trap holder configured to support a sample trap and a frame that secures said sample trap to the support surface.

6. The sampling device according to claim 5, wherein said sample trap is detachable from said trap holder.

7. The sampling device according claim 1, further comprising a force indicator configured to provide a sound upon application of a threshold amount of force on the target surface by said sampling device.

8. The sampling device according to claim 1, wherein said sampling device transitions into a threshold configuration when a threshold amount of force is applied to the target surface.

9. The sampling device according to claim 8, wherein the sampling device includes an over-force indicator that indicates when a predetermined amount of force that is greater than the threshold amount of force has been applied.

10. The sampling device according to claim 1, wherein said biasing member is a spring configured to remain in an at rest configuration when no force is applied to the target surface by said sampling device.

11. The sampling device according to claim 10, wherein said spring comprises at least one of a leaf spring, an extension spring, a torsion spring, a compression spring, a disc spring, an air spring, a gas spring, a flat spring, an elastomeric spring, or a constant force spring.

12. The sampling device according to claim 9, wherein the predetermined amount of force is within a range of about three to about five pounds of force.

13. The sampling device according to claim 1, further comprising a force indicator configured to visually indicate when a threshold amount of force is applied to the target surface by said sampling device.

14. The sampling device according to claim 1, further configured to provide tactile feedback to indicate that a threshold amount of force is applied to the target surface by said sampling device.

15. A method of using a mechanical force feedback sampling device, said method comprising:
grasping a handle of a sampling device;
applying a force against a target surface using the sampling device;
increasing the applied force to a threshold amount of force such that a mechanical force feedback mechanism induces a change in the orientation of the sampling device; and
collecting a sample, wherein the mechanical force feedback mechanism is configured to change an orientation of said body in relation to the handle when force is applied to the target surface by the sampling device, wherein the mechanical force feedback mechanism is defined by a rotational junction connecting the body to the handle, wherein the rotational junction comprises a cavity defined in an interior of one of the handle and the body, an arm extending from the other of the handle and the body and into the cavity, and a biasing member extending between the arm and an interior wall defining the cavity, and wherein the arm rotates in relation to the interior wall when force is applied to the target surface by the sampling device.

16. The method according to claim 15, wherein collecting a sample comprises collecting a sample using a sample trap, said method further comprising: inserting the sample trap into an analysis device for analysis of the sample.

17. The method according to claim 15, wherein increasing the applied force to a threshold amount of force comprises increasing the applied force to at least about a half pound of force.

18. A sampling device for collecting a sample from a target surface, said sampling device comprising:
a handle;
a body comprising an end, wherein the body is coupled to the handle;
a sampling head opposite said handle, said sampling head comprising a support surface configured to support a sampling trap; and
a mechanical force feedback mechanism configured to indicate when a threshold amount of force is applied to the target surface by the sampling device, wherein the mechanical force feedback mechanism is configured to change an orientation of the body in relation to the handle when force is applied to the target surface by the sampling device, wherein the mechanical force feedback mechanism is defined by a rotational junction connecting the body to the handle, wherein the rotational junction comprises a cavity defined in an interior of one of the handle and the body, an arm extending from the other of the handle and the body and into the cavity, and a biasing member extending between the arm and an interior wall defining the cavity, and wherein the arm rotates in relation to the interior wall when force is applied to the target surface by the sampling device.

* * * * *